United States Patent [19]

Zwick

[11] Patent Number: 4,543,481
[45] Date of Patent: Sep. 24, 1985

[54] LEAK DETECTION IN PIPELINES

[75] Inventor: Harold H. Zwick, Mississauga, Canada

[73] Assignee: Moniteq Ltd., Concord, Canada

[21] Appl. No.: 559,945

[22] Filed: Dec. 8, 1983

[51] Int. Cl.⁴ .............................................. G01J 1/00
[52] U.S. Cl. ................................................. 250/339
[58] Field of Search ...................... 250/341, 339, 343; 356/437

[56] References Cited

U.S. PATENT DOCUMENTS

| 3,783,284 | 1/1974 | McCormack | 250/341 |
| 3,976,884 | 8/1976 | Acton et al. | 250/343 |
| 4,013,260 | 3/1977 | McClatchie | 250/343 |
| 4,390,785 | 6/1983 | Faulhaber et al. | 250/330 |
| 4,489,239 | 12/1984 | Grant et al. | 250/339 |

OTHER PUBLICATIONS

Murray et al., "Remote Measure. of HCl, CH₄, and N₂O . . . ", Applied Optics, vol. 15, No. 12, Dec. 1976, p. 3140.

Primary Examiner—Alfred E. Smith
Assistant Examiner—Richard Hanig
Attorney, Agent, or Firm—Ridout & Maybee

[57] ABSTRACT

Leaks in natural gas pipelines are detected by an airborne gas cell correlation radiometer having two channels, one to detect methane and the other to detect nitrous oxide. The channel outputs are compared in order to detect anomalies in their relative magnitude, an increase in methane concentration relative to nitrous oxide concentration being indicative of a gas leakage in the area from which the radiometer receives radiation.

18 Claims, 3 Drawing Figures

LEAK DETECTION IN PIPELINES

FIELD OF THE INVENTION

This invention relates to the detection of leaks in gas pipelines, and to a radiometer suitable for that purpose.

BACKGROUND OF THE INVENTION

In a research paper co-authored by the present inventor and entitled "Quantitative Remote Sensing Tools for Air and Surface Measurements" presented and published at the Aug. 30, 1982 meeting of the International Society of Photogrammetry and Remote Sensing, there is included an outline description of a gas pipeline leak sensing instrument designed to detect methane and ethane leaking from natural gas pipelines. In this apparatus, incoming light is gathered by lenses and passed in two optical channels through a gas cell chopper wheel and band limiting interference filters onto cryogenically cooled infrared detectors. One optical train is used to detect methane, using a filter centred on a 7.8$\mu$ wavelength, and the other is used to detect ethane, using a filter centred on a 12.2$\mu$ wavelength. This radiometer makes use of a gas filter correlation technique, the chopper wheel containing a spectrally neutral filter, and cells containing samples of the gas to be detected.

The signals picked up by such a radiometer are considerably influenced by background radiation from the earth, atmospheric conditions, and fluctuations in the height above ground of an aircraft in which the instrument is flown caused by surface topography or other reasons. In theory, fluctuations in sensor output due to each of these causes can be compensated for, but in practice simultaneous compensation has proved difficult. Since methane is naturally present in the atmosphere at measurable concentrations, there are problems in distinguishing fluctuations in the methane signal due to leaks from fluctuations due to other causes, whilst typical ethane signals are often too small to detect with sufficient reliability.

SUMMARY OF THE INVENTION

With a view to overcoming these problems and providing a practical means for airborne leak detection in natural gas pipelines, I have now developed a new method and apparatus for detecting such leaks, and an improved radiometer which may be used in such apparatus.

According to the invention a method of detecting leaks in a gas pipeline comprises conveying an airborne radiometer along the route of the pipeline, focusing radiation from the vicinity of the pipeline upon the radiometer, sensing components of the radiation characteristic of two different gases, both of which are diffused through the atmosphere in low concentrations, but only one of which is present in the pipeline, determining the relative magnitude of these components, and detecting and recording changes in said relative magnitude as an indication of the presence of leaks.

A preferred version of the method further comprises simultaneously focusing radiation, from the same vicinity as the radiation focused upon the radiometer, to form images upon the pickup device of a television camera, and recording signals representing said images upon the same medium as said changes in relative magnitude, whereby to facilitate subsequent location of leaks indicated by such changes. Preferably the gases detected are $CH_4$ and $N_2O$.

The invention also extends to apparatus for detecting leaks in a gas pipeline, comprising a multiple channel radiometer mountable in or on an aircraft, means for focusing radiation on the radiometer from a defined direction beneath the aircraft, means for comparing the outputs of the channels of the radiometer to provide signals representative of changes in the relative magnitude of said outputs, and means to record said signals, one of said two channels being sensitive to radiation components characteristic of a first gas diffused at a low concentration through the atmosphere and also present in the pipeline, and the second channel being sensitive to radiation components characteristic of a second gas diffused at a low concentration through the atmosphere but not present in the pipeline. The radiometer is preferably a correlation gas filter cell radiometer, and the gases detected are preferably $CH_4$ and $N_2O$. These gases are both naturally present in the atmosphere at similar levels of concentration, and both exhibit marked absorption at similar wavelengths in the 7–8 micron band. Thus the atmospheric concentrations of both gases will provide background signals of a similar order of magnitude and with similar response to the various factors considered above. The absolute magnitude of the background signals may vary, but their relative magnitude should remain substantially the same. If the relative magnitude of the methane signal increases substantially, then this is indicative of some non-atmospheric source of methane such as a pipeline failure. The provision of an associated television recording enables easy subsequent location of a leak identified on review of the radiometer output record.

IN THE DRAWINGS

Figure 1:
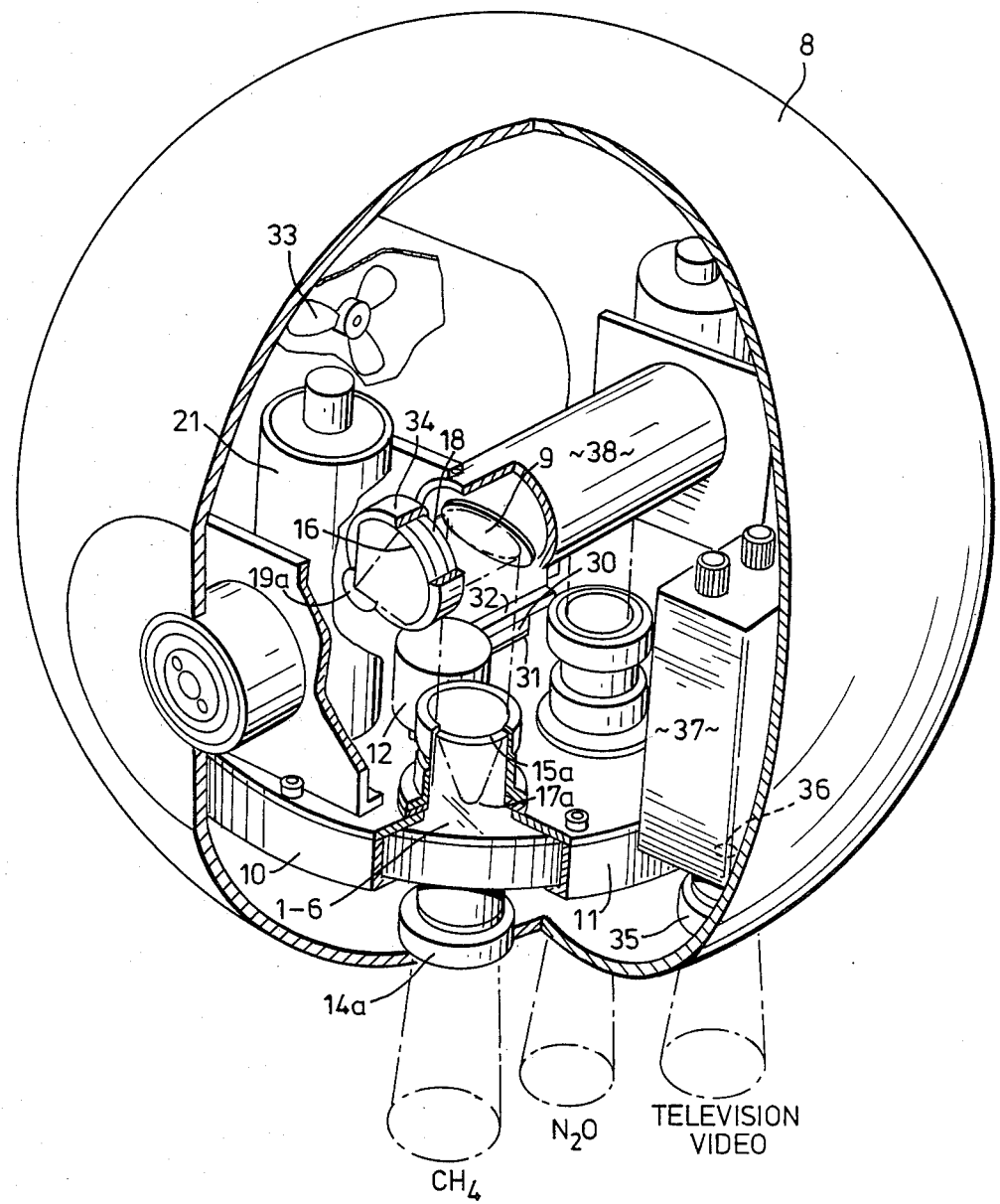
FIG. 1 is a perspective view of an exemplary embodiment of apparatus in accordance with the invention, suitably broken away to illustrate the internal construction.

Referring to FIG. 1, optical and transducing portions of the apparatus are shown enclosed in a generally spherical case 8 designed for pivotal mounting beneath an aircraft so that parallel optical axes of three lenses of which only lenses 14a and 35 can be seen located in openings in the bottom of the casing may be directed towards the path of a pipeline over which the aircraft is flown. Such a casing for aerial survey equipment is well known in the art and will not be described further. The lens 35 focuses an image of terrain beneath the aircraft on the pickup device 36 of a television camera 37, the video signal from which is recorded on a video recorder 56 (see FIG. 3). An audio frequency channel of this video recorder is also used to record output signals from a two channel radiometer described further below, the recorded video signal being utilized for subsequent location of anomalies detected by the radiometer. Conventional video recording techniques may be used and thus further description is believed unnecessary.

Figure 2:
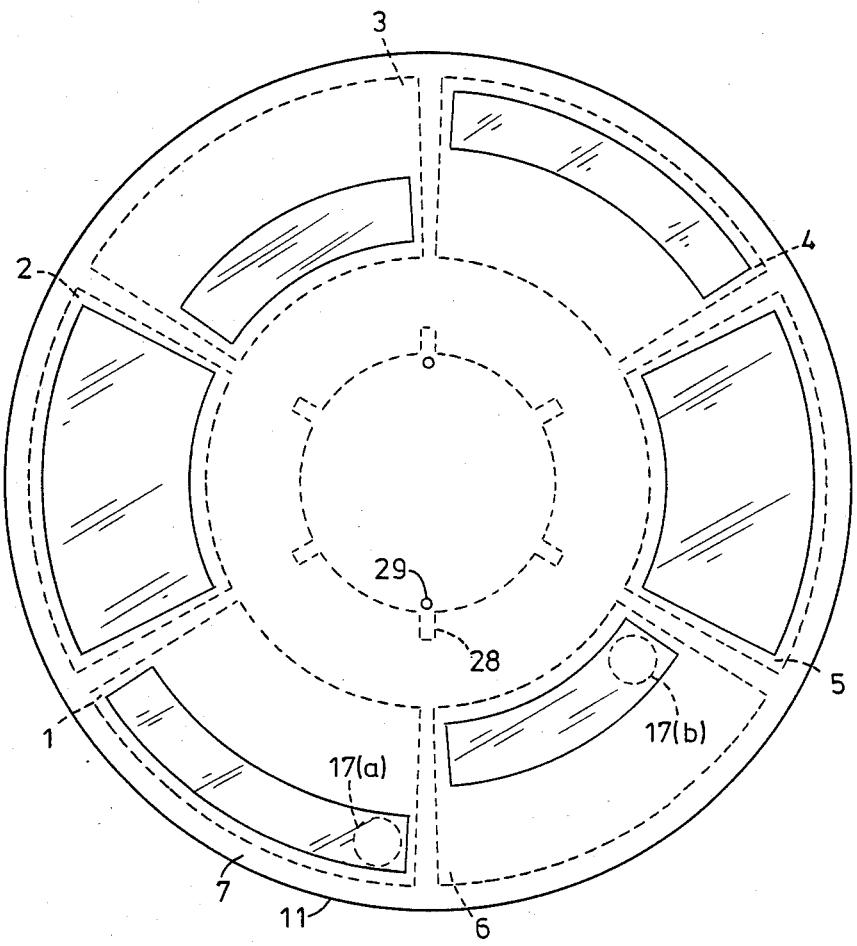
FIG. 2 is a plan view of a chopper disc incorporated into the apparatus.

The lenses 14a and 14b are each associated with one channel of a two channel radiometer, light entering the radiometer through lens tubes connecting the lenses to field stops 17a and 17b (see FIG. 2) in the bottom of a hermetically sealed housing 10 so as to fall on the lower surface of a chopper wheel 11 at angularly and radially spaced locations. The housing 10 is surrounded by insulation, and maintained at a substantially constant temperature by thermoelectric coolers 30 attached to the wall of the housing, the coolers being electrically controlled by signals derived from a temperature sensor 31 by means of a cooler control circuit 60 (See FIG. 3). Heat from the thermoelectric cooler is dissipated by means of a heat sink 32 and a blower fan 33. Typically, the temperature within the housing is controlled to a predetermined temperature $\pm 0.5°$ K.

The chopper wheel 11 (see also FIG. 2) is rotated within the housing by a motor 12. It is important that the rotational velocity of the wheel is accurately controlled and subject to no more than slight jitter. Typically, the motor is a four pole brushless DC motor driving the wheel directly, its angular position being sensed by a chopper wheel position sensor utilizing a pick-off comprising reflective marks 28 on a disc mounted on the wheel, an interface comprising optical sensors 29, and a feedback control circuit (see FIG. 5) comprising a timing interface 43 and a motor speed controller 36. The signals from the optical sensors 29 are also processed by the timing interface to provide clock signals indicative of the position of the sectors of the wheel 11 relative to the stops 17a and 17b.

The wheel 11 comprises an aluminum disc formed with a hub, a rim, and six equidistant spokes together defining six recesses within the disc, which receive gas cells, 1, 2, 3, 4, 5 and 6. A mask 7, typically of high emissivity paint, is applied to one surface of the wheel so as to restrict the effective area of cells 1, 3, 4 and 6 such that radiation passing the stop 17a cannot pass cells 3 and 6, and radiation passing the stop 17b cannot pass cells 1 and 4. Radiation from both stops can pass cells 2 and 5, which are filled with gas optically neutral to radiation at wavelengths of interest. Cells 1 and 4 contain samples of a first gas to be detected by a first channel of the radiometer, and cells 3 and 6 contain samples of a second gas to be detected by a second channel of the radiometer. The gas concentration in each cell 1, 3, 4 and 6 is optimized to maximize the effect on the transmitted radiation of the wavelengths of interest. As the wheel 11 rotates, radiation from the stop 17a will successively pass through a sample of the first gas, pass through the neutral gas, and be masked, with two complete cycles for each rotation of the wheel, thus increasing the chopping rate for a given rotational velocity of the wheel. Likewise, light from the stop 17b will successively pass through a sample of the second gas, be blanked, and pass through the neutral gas.

Radiation passing the wheel 11 from the stops 17a and 17b is collimated by lenses of which only lens 15a can be seen in FIG. 1 and thence falls on inclined oppositely facing mirrors 9 (only one of which is shown) located on a horizontal pivotal axis of the casing 8 by a housing 38, the mirrors being disposed to direct radiation from the stops 17a and 17b respectively horizontally outwards towards detector assemblies 21a and 21b mounted in the casing 8 by journals 39 connected to the aircraft structure so that the assemblies may be maintained vertical as the casing is tilted about its horizontal axis so as to direct the axes of the lenses 14a, 14b and 35 in a desired direction.

Light from the mirror 9 enters the detector assembly 21a through an interference filter 18a and is focused by a lens 16a on a photoconductive HgCdTe detector 19a mounted on the inner wall of the vacuum chamber of a Dewar flask filled with liquid nitrogen to maintain the detector at the proper temperature. The filter 18a is selected so as to pass only radiation within a selected passband. The other assembly 21b is similar, except that the filter is selected to have a passband appropriate to the gas being tested for in that channel.

Figure 3:
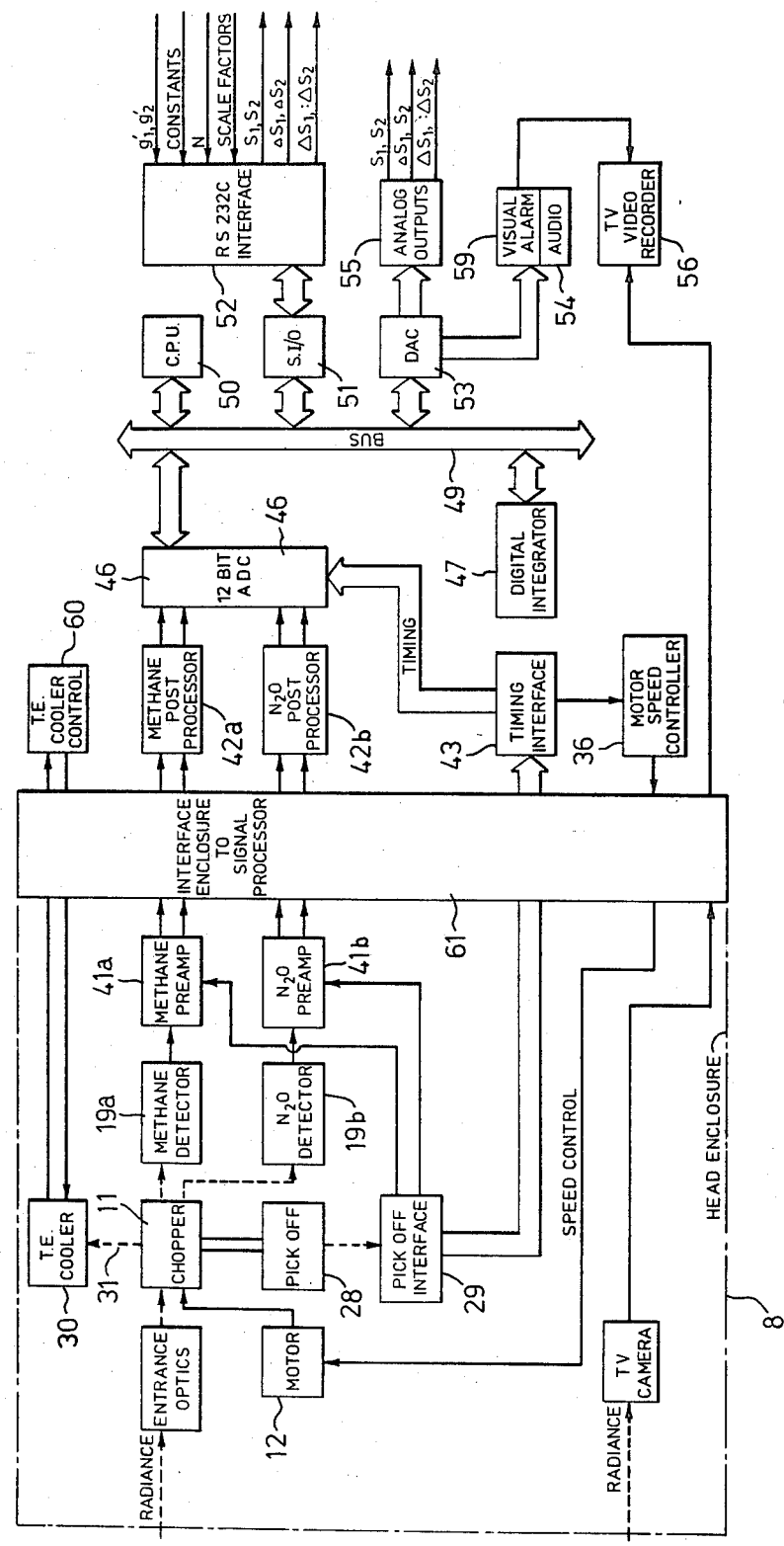
FIG. 3 is a block diagram of a signal processing circuit forming part of the apparatus.

Referring to FIG. 3, the detector output from each detector 19a and 19b is coupled to a preamplifier 41a or 41b (depending on the channel), and the amplified signal brought to a signal processor inboard of the aircraft by a suitable cable interface 61 together with the video signal from the camera 37 and power and signals to and from the cooler 30, the motor 12 and the pick-off interface 29. The signals from the preamplifiers are processed in separate channels comprising post-processors 42a and 42b. The two channels are then applied to an analog/digital converter 46 such that samples are generated from the photodetector outputs generated by each cell in the wheel 11, i.e. six cell samples per channel per revolution. The digitized signals are applied to a digital integrator 47 which integrates a number N of successive samples from each cell sector in each channel, thus filtering out high frequency noise and increasing resolution. Thus not only is noise immunity increased, but, for example, the resolution of a 16 bit A/D converter can be obtained from a 12 bit A/D converter. The digital integration is carried out under control of a microprocessor (C.P.U.) 50 via a data, address and control bus 49 to which various interface devices are connected, including the integrator 47. Various operations controlled by the microprocessor are timed by clock pulses derived from signals generating by the timing interface 43 from signals provided by the optical sensors of the interface 29. The signals generated by the timing interface also control motor 12, the signal processing steps carried out by the circuit 46, and other circuits yet to be described.

The first signal processing function performed in the microprocessor 50 is to interpolate the sample cell, spectral cell and blank sector signals to a common temporal point in time. This has the results of removing error signals which would otherwise result because of rapidly varying input light levels as the sensor footprint moves forward under the aircraft.

In addition, a gain control operation is performed in the microprocessor 50, which provides a multiplication of the data outputs of the integrator 47, with gain control data input through an RS-232C interface 52 and serial input/output adaptor 51 during a calibration operation; this interface is also used to load other operating constants and scale factors such as the number N. In the first channel, a gain factor 1.0 or $g_1$ is selected according to whether the integrator data output relates to an optically neutral cell 2 or 5 or the sample cell 1 or 4. In the second channel a gain factor 1.0 or $g_2$ is selected according to whether the integrator data output relates to optically neutral cells 2 or 5 or the sample cell 3 or 6. The gain corrected data for each channel is then processed by 50 to obtain a radiance signal S by differencing the neutral cell signals from the blank sector signals (corresponding to the sample cells of the other channel) and a difference signal $\Delta S$ by differencing the signals from the neutral reference cells and the gain corrected sample cells. This difference signal is proportional to the concentration C of the gas to be detected in the sensor field of view, in accordance with the expression $$\Delta S = aCL[B(T_g) - \epsilon B(T_s)]$$

where a is the absorption coefficient of the gas to be detected, which is a constant, L is the optical path length from the lens 14a or 14b to the ground, B(Tg) is the atmospheric gas temperature function, e is the ground emissivity, and B(Ts) is the ground surface temperature. However, for gases present in a similar order of concentration and having absorption maxima in the same range of wavelengths, the variables L, B(Tg) $\epsilon$ and B(Ts) will remain substantially equal for both channels. The ratio of the $\Delta S$ signals $\Delta S_1$ and $\Delta S_2$ from the two channels will thus be substantially independent of these variables. Any substantial change in this ratio is therefore indicative of an abnormal ratio of the concentrations of the two gases in the atmosphere.

The differencing operations are carried out by the microprocessor 50 under suitable program control for successive groups of signals generated by the integrator 47, and data representative of the signal $\Delta S_1/\Delta S_2$ and any of $S_1$, $S_2$, $\Delta S_1$ and $\Delta S_2$ may be output for recording or signalling purposes either in digital form, for example via the interface 52, or in analog form using a digital to analog converter 53 and interface 55. The analog signals so obtained may be also used to frequency modulate an audio frequency carrier or carriers which is or are recorded on an audio channel or channels of the video recorder 56 which records the video signals from the camera 37. An alarm 59 is provided to indicate when the $\Delta S_1/\Delta S_2$ signal deviates from its normal value by more than a predetermined tolerance.

In practice it is preferred that the two channels of the radiometer be configured to detect methane ($CH_4$) and nitrous oxide ($N_2O$) respectively, these gases being used to provide the sample gas in the cells 1 and 4 and 3 and 6 respectively, and the interference filters 14a and 14b being selected to pass wavelengths corresponding to the respective absorption maxima of these two gases in the 7–8 micron band. Since both gases are naturally present diffused through the atmosphere in concentrations of the same order of magnitude, the various variables which can effect the output signals from the detectors 19a, 19b will act equally on both channels, and thus do not mask anomalies in the relative concentrations of the two gases.

Thus the apparatus may be flown along the path of a buried or surface pipeline, and any leakage from the pipeline will cause a locally increased methane concentration which should be detected by the device, since there will be no corresponding increase in nitrous oxide concentration, the latter not being present in significant quantities in natural gas. The tape from the video recorder may be played back subsequently to relate gas concentration anomalies recorded at audio frequency with images of the location recorded from the television camera.

Whilst the apparatus has been described in relation to the airborne detection of leaks in pipelines, it will be appreciated that it may be utilized in other analogous applications for the fixed or mobile remote detection of anomalous gas concentrations in the atmosphere.

I claim:

1. A method of detecting leaks in a gas pipeline; comprising conveying an airborne radiometer along the route of the pipeline, focusing radiation from the vicinity of the pipeline upon the radiometer, sensing components of the radiation characteristic of two different gases, both of which are diffused through the atmosphere in low concentrations, but only one of which is present in the pipeline, determining the ratio of these components, and detecting and recording changes in said ratio as an indication of the presence of leaks.

2. A method according to claim 1, further comprising simultaneously focusing radiation, from the same vicinity as the radiation focused upon the radiometer, to form images upon the pickup device at a television camera, and recording signals representing said images upon the same medium as said changes in ratio, whereby to facilitate subsequent location of leaks indicated by such changes.

3. A method according to claim 1, wherein the gases detected are $CH_4$ and $N_2O$.

4. Apparatus for detecting leaks in a gas pipeline, comprising a multiple channel radiometer mountable in or on an aircraft, means for focusing radiation on the radiometer from a defined direction beneath the aircraft, means for comparing two outputs of the channels of the radiometer to provide signals representative of changes in the ratio of said outputs, and means to record said signals, one of said two channels being sensitive to radiation components characteristic of a first gas diffused at a low concentration through the atmosphere and also present in the pipeline, and the second channel being sensitive to radiation components characteristic of a second gas diffused at a low concentration through the atmosphere but not present in the pipeline.

5. Apparatus according to claim 4, further comprising means for focusing radiation from said direction to form images upon the pickup device of a television camera whereby to generate an image signal output and means to record said image signal output on the same medium as said signals representative of the ratio of the radiometer channel outputs.

6. Apparatus according to claim 4, wherein the radiometer is a correlation gas filter cell radiometer having channels for the detection of at least two different gases.

7. Apparatus according to claim 6, wherein the correlation gas filter cell radiometer has two channels, one for detection of absorption at a wavelength characteristic of $CH_4$ and the other for the detection of absorption at a wavelength characteristic of $N_2O$.

8. Apparatus according to claim 6, wherein the radiometer defines two independent optical paths for the radiance focused upon the radiometer, the two paths intersecting a chopper wheel at different radial distances from its rotational axis, and the chopper wheel comprising a ring of gas cells disposed in successive sectors of the wheel, which successively intersect the optical paths as the wheel rotates, together with a mask such that each optical path intersects only selected cells and is cut off by the mask from intersecting the other cells, the cells comprising cells containing respectively a first gas to be detected by a first channel, a second gas to be detected by a second channel, and an optically neutral gas, and the mask being disposed so one optical path intersects only the cells containing the first gas and the neutral gas, and the second optical path intersects only the cells containing the second gas and the neutral gas.

9. Apparatus according to claim 8, wherein there is a plurality of cells of each type.

10. Apparatus according to claim 8, wherein the first gas is $CH_4$ and the second gas is $N_2O$.

11. Apparatus according to claim 8, wherein the optical paths extend from an input lens and through the chopper wheel on parallel and nominally upwardly extending axes, and then in opposite directions on a common horizontal axis to independent detectors, one for radiance at a wavelength at which the first gas has an absorption maximum, and the other for radiance at a wavelength at which the second gas exhibits an absorption maximum.

12. Apparatus according to claim 11, wherein the radiometer is enclosed within a housing having stationary journals mounting it for pivotal motion about said horizontal axis, whereby to direct said lenses in a desired direction, the detectors being supported on said journals whereby to maintain their orientation during pivotal movement of the housing.

13. Apparatus according to claim 12, wherein the detectors are cryogenically cooled.

14. Apparatus according to claim 12, wherein the housing also contains a television camera, lenses of the television camera and the optical paths of the radiometer being directed in the same direction.

15. In a correlation gas filter cell radiometer in which the radiometer defines two independent optical paths for the radiance focused upon the radiometer, the two paths intersecting a chopper wheel a different radial distances from its rotational axis, and the chopper wheel comprising a ring of gas cells disposed in successive sectors of the wheel, which successively intersect the optical paths as the wheel rotates, together with a mask such that each optical path intersects only selected cells and is cut off by the mask from intersecting the other cells, the cells comprising cells containing respectively a first gas to be detected by a first channel, a second gas to be detected by a second channel, and an optically neutral gas, and the mask being disposed so one optical path intersects only the cells containing the first gas and the neutral gas, and the second optical path intersects only the cells containing the second gas and the neutral gas, the improvement wherein the optical paths extend from an input lens and through the chopper wheel on parallel and nominally upwardly extending axes, and then in opposite directions on a common horizontal axis to independent detectors, one for radiance at a wavelength at which the first gas has an absorption maximum, and the other for radiance at a wavelength at which the second gas exhibits an absorption maximum.

16. A radiometer according to claim 14, wherein the radiometer is enclosed within a housing having stationary journals mounting it for pivotal motion about said horizontal axis, whereby to direct said lenses in a desired direction, the detectors being supported on said journals whereby to maintain their orientation during pivotal movement of the housing.

17. A radiometer according to claim 14, wherein the first gas is $CH_4$ and the second gas is $N_2O$.

18. A radiometer according to claim 14, wherein there is a plurality of cells of each type.

* * * * *